(12) United States Patent
Schönlein

(10) Patent No.: US 7,353,722 B2
(45) Date of Patent: Apr. 8, 2008

(54) CONTACTLESS MEASUREMENT OF THE SURFACE TEMPERATURE OF NATURALLY OR ARTIFICIALLY WEATHERED SAMPLES

(75) Inventor: Artur Schönlein, Rüsselsheim (DE)

(73) Assignee: Atlas Material Testing Technology GmbH (DE)

(*) Notice: Subject to any disclaimer, the term of this patent is extended or adjusted under 35 U.S.C. 154(b) by 20 days.

(21) Appl. No.: 10/943,142

(22) Filed: Sep. 17, 2004

(65) Prior Publication Data
US 2005/0092114 A1    May 5, 2005

(30) Foreign Application Priority Data
Sep. 18, 2003   (DE)   ................. 103 43 280

(51) Int. Cl.
*G01N 17/00* (2006.01)
(52) U.S. Cl. ............... 73/865.6; 250/492.1; 374/45; 374/57; 702/134; 702/135; 702/150; 702/151
(58) Field of Classification Search .............. 73/865.6, 73/866; 374/9, 43, 44, 57, 100, 120, 121, 374/132, 141; 702/130–136, 150, 151
See application file for complete search history.

(56) References Cited

U.S. PATENT DOCUMENTS

| | | | | |
|---|---|---|---|---|
| 3,709,026 A | * | 1/1973 | Rhodes et al. | 73/12.11 |
| 4,634,294 A | * | 1/1987 | Christol et al. | 374/170 |
| 4,704,903 A | * | 11/1987 | Suga et al. | 73/159 |
| 4,760,748 A | * | 8/1988 | Katayanagi et al. | 73/865.6 |
| 4,874,952 A | * | 10/1989 | Arnaud et al. | 250/455.11 |
| 4,924,478 A | * | 5/1990 | Tank | 374/121 |
| 4,957,011 A | * | 9/1990 | Huber et al. | 73/865.6 |
| 5,138,892 A | * | 8/1992 | Suga | 73/865.6 |
| 5,219,226 A | | 6/1993 | James | |

(Continued)

FOREIGN PATENT DOCUMENTS

EP    0 320 209    6/1989

(Continued)

OTHER PUBLICATIONS

Boisseau et al., "Accelerated Acid Etch for Automotive Clearcoats", 2004, FSCT 82nd Annual Meeting Technical Program.*

(Continued)

*Primary Examiner*—Hezron Williams
*Assistant Examiner*—David A. Rogers
(74) *Attorney, Agent, or Firm*—Vedder Price, P.C.

(57) ABSTRACT

A holding frame (2) is mounted in a weathering chamber (1) of a weathering tester so that it can be rotated around a xenon radiation source (3), which is located on the cylinder or rotation axis, and an infrared filter (5) placed around it. Samples (3) to be weathered are fastened to the inside of the holding frame (2) and are exposed to the radiation from the xenon radiation source (4). The surface temperature of the samples (3) can be recorded directly by a black-body radiation detector such as a pyrometer (6), which is aimed at a stationary region of space through which the samples (3) pass periodically during their rotational movement. The surface temperature can be computed in an evaluation circuit from the detected black-body radiation, together with emissivity values stored for the individual samples (3).

9 Claims, 1 Drawing Sheet

U.S. PATENT DOCUMENTS

Figure 1A:
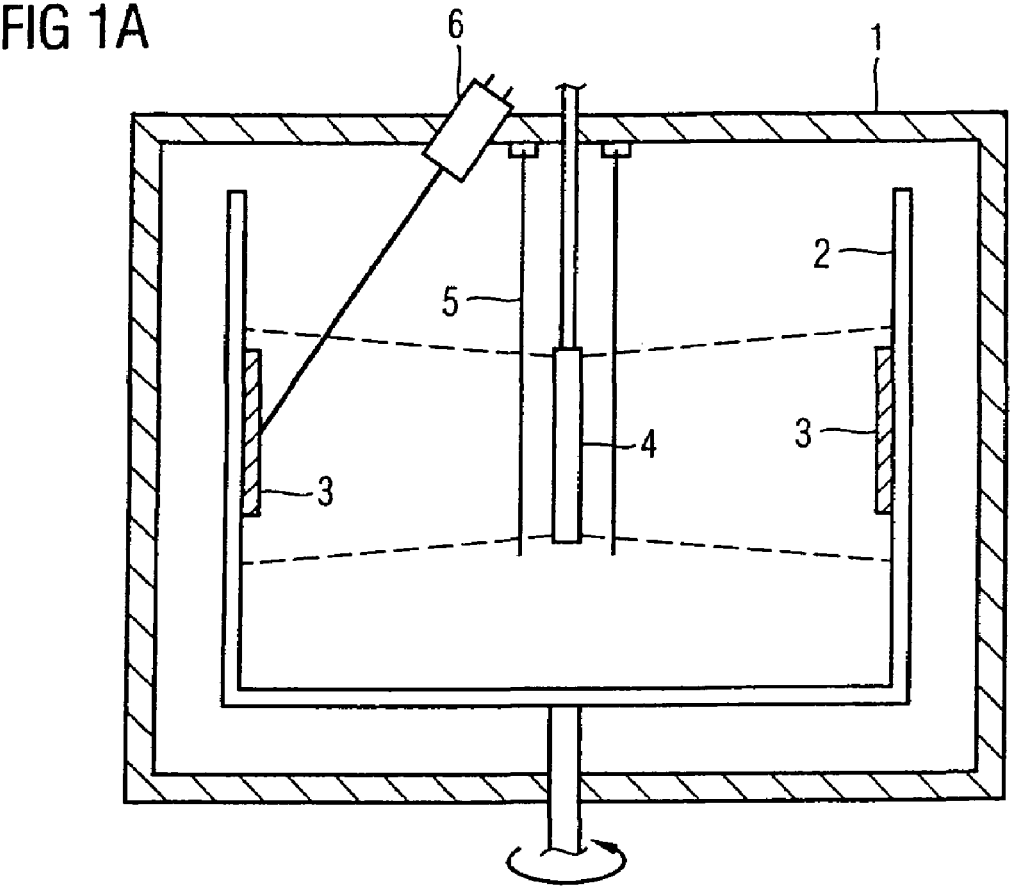

| | | | |
|---|---|---|---|
| 5,305,634 A * | 4/1994 | Suga et al. | 73/86 |
| 6,423,949 B1 | 7/2002 | Chen et al. | |
| 6,626,052 B1 * | 9/2003 | Martin et al. | 73/865.6 |
| 6,892,591 B2 * | 5/2005 | Grossman et al. | 73/865.6 |
| 2002/0139928 A1 * | 10/2002 | Rathod et al. | 250/252.1 |
| 2002/0189377 A1 * | 12/2002 | Beraud | 73/865.6 |

FOREIGN PATENT DOCUMENTS

| | | | |
|---|---|---|---|
| FR | 2430609 A * | 3/1980 | |
| JP | 61-105444 | 5/1986 | |
| JP | 63-61935 | 3/1988 | |
| JP | 9-166542 | 6/1997 | |
| JP | 09-329498 | 12/1997 | |

OTHER PUBLICATIONS

"Black Body", Wikipedia Online, <http://en.wikipedia.org/wiki/Blackbody>.*

"Quantification and Prediction for Aging of Printing & Writing Papers Exposed to Light" 2000, United States Department of Agriculture Forest Service, pp. 1-151.*

Brown, et al., "Development of Humidity Recommendations in Museums and Moisture Control in Buildings", 1997, pp. 1-28.*

Wypych, George, "Handbook of Material Weathering", 2003, ChemTec Publishing, 3$^{rd}$ edition,pp. 365, 407, and 503.*

Aubin et al., "Natural and Artificial Weathering of EPDM Compounds Used in Outdoor High Voltage Insulation", Aug. 1981, IEEE Transactions on Electrical Insulation, vol. El-16, No. 4, pp. 290-296.*

Boxhammer J. et al., "Black Standard Thermometer", Materialoprüfung 35 (1993).

* cited by examiner

CONTACTLESS MEASUREMENT OF THE SURFACE TEMPERATURE OF NATURALLY OR ARTIFICIALLY WEATHERED SAMPLES

The present invention relates to a method for evaluating the weathering-dependent ageing of a sample, in which the sample is exposed to natural or artificial weathering. The invention also relates to a device for the artificial weathering of samples.

Devices for the artificial weathering of samples are intended to estimate the lifetime of materials which are constantly exposed to natural weathering conditions during their use, and which therefore suffer from climatic effects such as sunlight, solar heat, moisture and the like. In order to obtain a good simulation of the natural weathering situation, the spectral energy distribution of the light generated in the device should correspond as closely as possible to that of natural solar radiation, for which reason xenon radiators are used as radiation sources in such devices. An accelerated ageing test of the materials is essentially achieved by much more intense irradiation of the samples compared with natural conditions, which speeds up the ageing of the samples. In this way, a prediction of the long-term ageing of a material sample can be made after a comparatively short time.

A large number of the samples studied in artificial weathering devices consist of polymeric materials. Their deterioration due to weathering is essentially caused by the UV component of solar radiation. The primary photochemical processes which take place during this, that is to say the absorption of photons and the generation of excited states or free radicals, are independent of temperature. The subsequent reaction steps with the polymers or additives, however, may be temperature-dependent so that the observed ageing of the materials is also temperature-dependent. The degree of temperature dependency differs according to the material and the property whose variation is considered.

In order to accommodate this fact, the room temperature and/or the sample temperature are generally kept constant for the artificial weathering of polymeric materials. Owing to the temperature dependency of the ageing, it is necessary to have constant and known temperatures so that the results of different weathering experiments can be compared with one another.

Since the direct measurement of the sample temperature of the material samples to be studied has not been addressed in the past, temperature sensors whose measured temperature is used to reflect the sample temperature are used in weathering devices. For example, a black panel sensor may be used as such a temperature sensor. Patent Specification EP 0 320 209 A2 describes a weathering device which has a weathering chamber in which a xenon lamp is provided as the light source, in order to emit light with a predetermined intensity. The weathering chamber also contains a rotationally symmetric sample holder frame, which can be rotated around the light source. This sample holder frame carries both material samples to be studied and black panel sensors. The material samples and the black panel sensors are therefore exposed under the same conditions to the radiation field of the light source and the other prevalent conditions inside the weathering chamber. In order to be able to control the sample temperature within particular limits, and in order to homogenize it inside the weathering chamber, an air flow is also blown into the weathering chamber and, with rotational symmetry relative to the light source, it sweeps over the sample holder frame and the material samples and black panel sensors which the latter holds. The air flow dissipates some of the heat from the material samples and black panel sensors. This can be employed in order to regulate the temperature by using the temperature measured by the black panel sensors as a control signal for the strength of the air flow blown into the weathering chamber.

All of the black panel sensors, black standard sensors and white standard sensors used as temperature sensors are constructed so that they have a metal plate with a painted surface which faces the light source during operation, and a temperature-dependent electrical component thermally coupled to the back of the metal plate. The electrical component is generally formed by a thermistor such as a platinum resistor (commercial references Pt100 or Pt1000) and is connected to an electrical measuring transducer circuit.

Specifically, the conventional black standard sensor has a stainless steel plate (thickness 1 mm) painted black on one side, a Pt100 or Pt1000 resistor thermally coupled to the uncoated back, a PVDF (polyvinylidene fluoride) plastic plate applied to the back and enclosing the platinum resistor, and a stainless steel cover plate. A white standard sensor is constructed in a similar way, but the surface which faces the light source during operation is painted white. Unlike the black standard sensor, a black panel sensor consists of a metal plate blackened on both sides without any PVDF insulation. The thermistor is fitted on the back without insulation around it.

In conventional weathering devices according to the current standard, black standard or black panel sensors are used in order to be able to find a black standard temperature for each weathering process. The black standard temperature constitutes an upper limit for the relevant range of the surface temperature of the material sample. The white standard sensor is often used as well, and its temperature measurement provides a lower limit for this range. The sample temperature can thereby be delimited, and the arithmetic mean of the measured temperatures may optionally be taken as a first approximation for the sample temperature.

The disadvantage of this conventional temperature measuring method is that the surface temperature of the sample cannot be delimited precisely enough. The current requirements of comparability and reproducibility for weathering experiments entail stringent requirements on the accuracy of the temperature measurement. The conventional temperature measuring method does not fully meet these requirements.

It is therefore an object of the invention to increase the accuracy of the measurement of the surface temperature of naturally or artificially weathered samples during the weathering. claim 9.

The method according to the invention for evaluating the weathering-dependent ageing of a sample is suitable for both natural and artificial weathering methods. One important idea of the present invention to that of directly measuring the surface temperature of the sample during the weathering. This is facilitated by a contactless temperature measuring method.

Since the surface temperature of the sample is no longer delimited by aids such as black and white standard sensors, as it was in the past, but is determined by measurement from the sample itself, it is possible to measure the surface temperature more precisely during the weathering.

This also obviates the need to provide the said black or white standard sensors, or black panel sensors, and their elaborate calibration prior to use in a weathering tester.

The contactless temperature measuring method according to the invention may be carried out by recording the blackbody radiation of the sample surface and determining the surface temperature from the intensity and/or spectral distribution of the recorded black-body radiation. This may be done by using a commercially available pyrometer, which is calibrated at least in the measurement range corresponding to the temperature range of interest. The pyrometer can be used to fix a measuring spot on the sample surface, at a particular angle to the sample, and the black-body radiation emitted by this measuring spot in the corresponding solid angle can be recorded and the surface temperature determined therefrom.

If the contactless temperature measurement is carried out by measuring the black-body radiation, then in principle this presupposes that the radiation emission factor or the radiation emissivity of the surface material of the sample is known, since the sample's surface that emits the black-body radiation does not have the properties of an ideal black-body radiator ($\epsilon=1$) and the emissivity $\epsilon$ is always less than 1. The angular dependency of the emissivity of the sample material should also be known since, as mentioned above, it is the black-body radiation emitted by the pyrometer in a particular solid angle which is recorded.

In respect of the emissivity values of the samples and work-pieces to be weathered, on the one hand, it is possible to employ empirical values such as tabulated values from the literature. It is, however, also possible to determine the emissivities of the samples by a suitable method before the actual weathering. Since the genuine emissivity values of the samples are determined in this case, it allows very accurate determination of the surface temperature from the recorded black-body radiation.

Even if the emissivity of the sample material is not experimentally determined beforehand, and it is therefore not known accurately, the determination of the surface temperature can be approximated better from the recorded black-body radiation by using an assumed emissivity value than in the conventional method, in which only a relatively large range between an upper and lower temperature limit can be found by using black and white standard sensors.

In current devices for artificial weathering, a number of sample pieces to be weathered are generally fastened to a holding frame closed in a ring shape, to which a rotational movement is imparted around a centrally arranged radiation source such as a xenon radiator. A detector for recording the black-body radiation, for example a pyrometer, may be arranged therein so that it fixes a stationary measuring spot through which the samples move during their circular movement. Emissivity values are then stored for each sample, so that the surface temperature can be determined from their emitted black-body radiation and their emissivity. It may be preferable for the current angular position of the holding frame to be used in order to assign the black-body radiation recorded by the pyrometer to a particular sample. The emissivity value stored for this sample can then be used in order to determine the surface temperature from the recorded black-body radiation.

A device according to the invention for the artificial weathering of samples has a weathering chamber, which contains a radiation source and holding means to hold samples to be weathered, and a contactless temperature sensor. The contactless temperature sensor is, in particular, a black-body radiation detector such as a (calibrated) parameter.

The holding means may be formed, in a manner which is known per se, by a holding frame closed in a ring shape, which is arranged concentrically around a radiation source and to which a rotational movement around the radiation source can be imparted. The contactless temperature sensor is then preferably static and fixed in its alignment, so that it is aimed at a stationary region of space. One or more of the samples to be weathered, which are held in the holding frame, pass periodically through the stationary region of space during the rotational movement of the holding frame around the radiation source, and they are measured by the contactless temperature sensor each time they pass. In the case of a black-body radiation detector, black-body radiation of the sample is emitted in the direction of the black-body radiation detector each time a sample passes through the stationary region of space, and is recorded by it.

If the temperature sensor is a black-body radiation detector, then values for the radiation emissivity of the samples may be stored in an evaluation circuit connected to it. Each time the black-body radiation of a particular sample has been recorded, its intensity and/or spectral distribution is correlated with the associated emissivity value in order to give the surface temperature of the sample.

The sample currently located in the stationary region of space can be identified by using the angular position of the holding frame.

The present invention will be explained in more detail below with the aid of a single exemplary embodiment and with reference to the figures of the drawing.

Figure 1B:
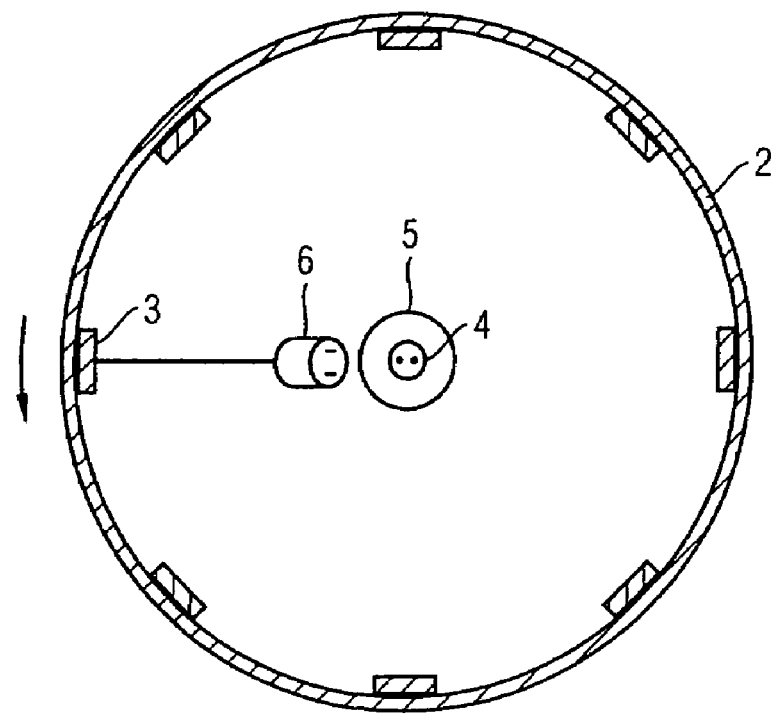

FIGS. 1a, 1b represent a weathering tester according to the invention in a longitudinal section (FIG. 1a) and in a plan view (1b).

A holding frame 2 closed in a ring shape is mounted so that it can rotate in a weathering chamber 1, and samples 3 or work-pieces can be held on its inner wall. The holding frame 2 has, in particular, a circular cross section. A xenon radiation source 4, which is fixed to an inner wall of the weathering chamber 1, is positioned on the cylinder and rotation axis of the holding frame 2. The xenon radiation source 4 is used to emit radiation comparable with natural solar radiation and to expose the samples 3 thereto. The xenon radiation source 4 is surrounded by a tubular filter 5 which is adapted to the weathering test in question.

In a manner which is known per se, the weathering chamber may also have other artificial weathering instruments, for example moisture generators or the like, although these do not play an essential part in the present invention and will not therefore be discussed in detail. And air flow may also be blown into the weathering chamber 1 and sweep past the samples 3 in a vertical direction.

The holding frame 2 is preferably mounted so that it can rotate, in such a way that the rotation axis coincides with the axis of the xenon radiation source 4 and so that the samples 3 essentially move on a circular path around the xenon radiation source 4 and at a constant distance from it.

In the exemplary embodiment which is shown, an opening into which a pyrometer 6 can be fitted from the outside is formed in the upper wall of the weathering chamber 1. As an alternative to this, the pyrometer may also be arranged at a suitable position fully inside the weathering chamber 1. The exemplary embodiment in FIG. 1a furthermore shows that the pyrometer 6 is aimed in a fixed position at a sample 3 and records the black-body radiation emitted by the latter. The black-body radiation is therefore always recorded by the pyrometer 6 at an oblique angle to the horizontal.

The pyrometer 6 is therefore fixed on a stationary region of space, through which the samples 3 pass periodically during their circular movement. It is clear from the plan view in FIG. 1b that the black-body radiation emitted by a sample 3 can therefore be detected by the pyrometer 6 in time intervals whose length is determined by the rotation speed of the holding frame 2 and the width of the sample 3. After the end of such a time interval, the surface temperature can be computed from the recorded black-body radiation in an evaluation circuit connected to the pyrometer 6, by using the emissivity stored for the respective sample 3. The emissivity values of the samples 3 fastened to the holding frame 2 may be stored in the evaluation circuit. After the black-body radiation has been recorded, it is first necessary to identify the sample 3 in order to be able to find the emissivity value stored for this sample 3. To that end, the angular position of the holding frame 2 may be determined in a suitable way, and a table may be compiled beforehand to show which of the samples 3 actually lie in the stationary measuring region of the pyrometer 6 for particular measured angular positions of the holding frame 2. After having thereby identified the sample 3 which emitted the black-body radiation within the measuring time window, the emissivity value corresponding to the sample 3 is correlated with the intensity and/or spectral distribution of the black-body radiation in order to obtain the surface temperature of the sample 3 therefrom.

The pyrometer 6 is preferably calibrated for a measurement region of between 8 µm and 14 µm in the temperature range of 20-120° C.

The surface temperature of each sample 3 is preferably recorded continually during the weathering test.

The method according to the invention may also be used in principle for other for natural weathering methods. Here again, the samples or work-pieces may be fastened to a holding frame and moved on a closed path past a temperature sensor such as a pyrometer, which obviates the need for the alignment of the pyrometer to be constantly changed in order to aim it at different samples.

The invention claimed is:

1. A method for evaluating the weathering-dependent ageing of a sample, comprising:
   exposing the sample in an enclosure to natural or artificial weathering, and
   contactlessly measuring a surface temperature of the sample during the weathering by measuring a black-body radiation of the sample surface and determining the surface temperature therefrom on the basis of an assumed or experimentally determined value of the radiation emissivity of the sample,
   wherein the sample is moved through space within the enclosure during the weathering, the black-body radiation is measured by using a pyrometer aimed at a stationary region of space and measuring the black-body from the stationary region of space, and the sample identified from an angular position of the holding frame is moved through the interior of the enclosure during the weathering in a way that the sample surface passes periodically through the stationary region of space and allowing the pyrometer to measure the black-body radiation during the passage time of the sample through the stationary region.

2. The method according to claim 1, wherein the blackbody radiation emitted by the surface in a defined oblique angle is measured.

3. The method according to claim 2, wherein for artificial weathering, the sample is moved on a closed path around a radiation source.

4. The method according to claim 3, wherein a number of samples, which are fastened to a holding frame closed in a ring shape, are weathered simultaneously.

5. The method according to claim 4, wherein
   radiation emissivity values for the samples are stored before the weathering, and
   the recorded black-body radiation and the radiation emissivity value stored for the sample are employed for the temperature calculation.

6. A device for the artificial weathering of samples, comprising:
   a weathering chamber which contains a radiation source and holding means to hold samples to be weathered;
   the holding means being formed by a holding frame closed in a ring shape, which is arranged concentrically around the radiation source and to which a rotational movement around the radiation source can be imparted,
   a pyrometer for contactlessly measuring the surface temperature of the samples by measuring the black-body radiation emitted from the surfaces of the samples, respectively, the pyrometer being aimed at a stationary region of space, wherein the holding frame is designed so that one or more held samples passes periodically through the stationary region of space during the rotational movement, and the pyrometer is designed so that it measures the black-body radiation of a particular sample identified from an angular position of the holding frame during the passage of time of the sample through the stationary region of space.

7. The device according to claim 6, wherein, values for a radiation emissivity of the samples can be stored in an evaluation circuit connected to the black-body radiation detector.

8. The device according to claim 6, wherein, the pyrometer is aimed at the sample or samples with an oblique angle to the horizontal.

9. A method for evaluating the weathering-dependent ageing of a sample, comprising:
   exposing the sample within an enclosure to natural or artificial weathering; and contactlessly measuring the surface temperature of the sample during the weathering with a stationary sensor placed,
   wherein the black-body radiation of the sample surface is recorded, and the surface temperature is determined therefrom on the basis of an assumed or experimentally determined value of the radiation emissivity of the sample, and wherein, the sample is moved through space during the weathering within the enclosure and is identified from an angular position of the holding frame, the black-body radiation from a stationary region of space is recorded, and the sample is moved so that its sample surface passes periodically through the stationary region of space.

* * * * *